US009483620B2

(12) United States Patent
Reimer (10) Patent No.: US 9,483,620 B2
(45) Date of Patent: Nov. 1, 2016

(54) REMINDER PROGRAMMING DEVICE AND METHOD

(75) Inventor: Soeren Dybdal Reimer, Birkeroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/639,267

(22) PCT Filed: Apr. 8, 2011

(86) PCT No.: PCT/EP2011/055562
§ 371 (c)(1),
(2), (4) Date: Apr. 18, 2013

(87) PCT Pub. No.: WO2011/124711
PCT Pub. Date: Oct. 13, 2011

(65) Prior Publication Data
US 2013/0253699 A1    Sep. 26, 2013

Related U.S. Application Data

(60) Provisional application No. 61/323,577, filed on Apr. 13, 2010.

(30) Foreign Application Priority Data

Apr. 9, 2010    (EP) .................................... 10159523

(51) Int. Cl.
*G08B 1/00*    (2006.01)
*G06F 19/00*    (2011.01)
(Continued)

(52) U.S. Cl.
CPC ....... *G06F 19/3462* (2013.01); *G06F 19/3468*
(2013.01); *A61J 7/049* (2015.05); *A61M 5/24*
(2013.01); *A61M 5/31551* (2013.01); *A61M 5/31585* (2013.01)

(58) Field of Classification Search
CPC ........ A61J 7/04; A61J 7/0409; A61J 7/0472;
A61J 7/0481; A61J 2007/0418; A61J 7/049;
A61M 2205/52; A61M 5/24; A61M 5/31551;
A61M 5/31585; G06F 19/3456; G06F
19/3462; G06F 19/3468
USPC ................. 340/309.16, 309.7, 573.1, 539.12
See application file for complete search history.

(56) References Cited

U.S. PATENT DOCUMENTS 4,617,557 A    10/1986    Gordon
5,088,056 A    2/1992    McIntosh
(Continued)

FOREIGN PATENT DOCUMENTS

CN    101489517 A    7/2009
JP    2004516108 A    6/2004
(Continued)

*Primary Examiner* — Thomas Mullen
(74) *Attorney, Agent, or Firm* — Wesley Nicolas (57) ABSTRACT

An electronically controlled reminder device is adapted to be set in a programming mode by a user, perform a user-actuated operation, and detect when a user-actuated operation is performed. When in programming mode the device is adapted to record and set reminders in accordance with a detected time pattern of operation(s) of the device, wherein the programming mode is activated for a pre-determined number of operations or for a pre-determined period of time, after which the device automatically returns to the operational mode in which it provides reminders to the user based on the recorded time pattern of operations. Thus, normal use of the device provides automatic programming of the reminder scheme.

10 Claims, 3 Drawing Sheets

(51) Int. Cl.
*A61M 5/24* (2006.01)
*A61M 5/315* (2006.01)

(56) References Cited

U.S. PATENT DOCUMENTS

| | | |
|---|---|---|
| 5,097,429 A | 3/1992 | Wood et al. |
| 5,861,797 A | 1/1999 | Becker |
| 7,170,823 B2 | 1/2007 | Fabricius et al. |
| 2003/0020599 A1* | 1/2003 | Somers et al. ........... 340/309.15 |
| 2003/0222090 A1* | 12/2003 | Abdulhay et al. ................ 221/3 |
| 2007/0220754 A1 | 9/2007 | Barbaro et al. |

FOREIGN PATENT DOCUMENTS

| | | |
|---|---|---|
| JP | 2008514249 A | 5/2008 |
| WO | 9938554 | 8/1999 |
| WO | 99/43283 | 9/1999 |
| WO | 02/056822 | 7/2002 |
| WO | 03/107291 A2 | 12/2003 |
| WO | 2006/069778 A2 | 7/2006 |

* cited by examiner

REMINDER PROGRAMMING DEVICE AND METHOD

CROSS-REFERENCE TO RELATED APPLICATIONS

This application is a 35 U.S.C. §371 national stage application of International Patent Application PCT/EP2011/055562 (published as WO 2011/124711), filed Apr. 8, 2011, which claimed priority of European Patent Application 10159523.9, filed Apr. 9, 2010; this application further claims priority under 35 U.S.C. §119 of U.S. Provisional Application 61/323,577, filed Apr. 13, 2010.

The present invention generally relates to electronically controlled systems and devices allowing event related information to be stored and used to remind a user of an action to be performed. In a specific embodiment the invention relates to a medical delivery device in combination with a user operated interface taking a dose of a given drug or perform an action, however, the different aspects of the present invention is applicable for all types of devices or systems in which a customized reminder function would be desirable. In an exemplary embodiment the invention is embodied in a pen-formed drug delivery device, however, the invention may be used in many other types of devices, e.g. medical aerosol inhalers, tablet dispensing devices and blood glucose meters etc.

BACKGROUND OF THE INVENTION

In the disclosure of the present invention reference is mostly made to the treatment of diabetes by injection of insulin, however, this is only an exemplary use of the present invention.

Lack of substantial patient compliance with established dosage intervals has long been recognized as a major problem in treating illness. Typically in treating a patient, a physician will desire the patient to take a needed drug on a specific schedule. The prescribed (or over-the-counter) medicine is usually obtained from a pharmacist, or the doctor himself, with the actual administration of the drug left to the sole control of the patient. However, even a well-meaning and conscientious patient may frequently fail to take medication at the desired dosage intervals. This may be true even if the medication is carried at all times with the patient.

Potential ill effects of lack of compliance with the desired dosage interval may be further compounded if the patient attempts to compensate for missed dosages by taking an increased dose at a later time. Alternatively, the patient may stop taking the medication altogether. Improper dosage may occur whenever the patient has a marginally impaired memory and may not precisely recall taking the medication or correctly judge how much time has elapsed since medicine was last taken.

Patients with diseases, specifically diabetes, which require regular and systematic self managed treatment regimes, are thus facing the challenge of remembering when to take their medication. Since such regimes can prescribe daily to weekly medication, which furthermore have to be personalised to accommodate the routines of the patient, e.g. meal times, working hours etc. Often patients develop individual, home-brewed, systems to remind them to take their medication.

As substantial non-compliance with a desired medication regimen is a major concern, the above problems have been addressed by a number of compliance aid devices which are adapted to provide an alarm or reminder in case a patient does not comply with a programmed schedule for taking a given dose of medicine.

For example, US 2007/0220754 discloses an electronically controlled pill bottle holder which can be programmed by the user to serve as a reminder when the pill bottle is not removed from the apparatus according to the programmed schedule. U.S. Pat. No. 7,170,823 discloses a medical dispenser in which the alarm functionality has been integrated into the dispenser. In a specific embodiment the dispenser is in the form of a pen device for subcutaneous injections of a drug, e.g. a diabetes drug or growth hormone, the pen comprising a main portion with a drug reservoir and a dosing mechanism as well as a cap portion comprising the electronic means for providing the alarm functionality.

WO 99/43283 discloses a pen device which can be programmed with two reminders by actuating a programming button which has to be operated in order to program the reminders.

When properly programmed these devices serve well to remind a patient that it is time to take his or her medication (or confirm that a given dose was taken or not taken), however, for many patients it may be an obstacle to properly program the device for which reason this type of compliance aid is never put in use despite the fact that it may well be very useful for a given patient when the initial difficulties of programming the device have been overcome. Such difficulty is often related to the ability to understand a complex user interface, when attempting to program a personalised reminder scheme.

Having regard to the above, it is an object of the present invention to provide an easy understandable and intuitive reminder programming functionality for an electronically controlled device. It is a further object to provide a user interface and device which can be realized in a simple and cost-effective manner.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect an electronically controlled device is provided, the device comprising processor means having an operational mode in which reminders can be generated, the processor means being adapted to be set in a programming mode by a user, perform a user-actuated operation, and detect when a user-actuated operation is performed. When in programming mode the device is adapted to record and set reminders in accordance with a detected time pattern of operation(s) of the device, wherein the programming mode is activated for a pre-determined number of operations or for a pre-determined period of time, after which the device automatically returns to the operational mode in which it provides reminders to the user based on the recorded time pattern of operations. As appears, normal use of the device provides automatic programming of the reminder scheme, the only "extra" operation left to the user is to bring the device into programming mode. Especially, the user no longer has to leave the programming mode as this function is provided automatically in accordance with the set-up of the device, this in contrast to known devices which requires specific and additional user-operations to program reminders.

The present invention may be embodied in a number of different devices in which it is relevant to set and provide reminders, e.g. drug delivery devices, medical aerosol inhalers, tablet dispensing devices and blood glucose meters etc. Depending on the type of device and the functionality provided by the device, the kind of user-actuated operation will vary. For example, the operation may be associated with the simple task of "starting" the device, e.g. taking off a cap, flipping a cap or actuating an on-button. Alternatively, the operation may be associated by "real" use of the device, e.g. setting a dose of drug, expelling a dose of drug, or determining a BG value.

In the context of the present application and as used in the specification and claims, the term electronically controlled device indicates that the device is provided with processor means which may be in the form of any combination of electronic circuitry suitable for providing the specified functionality, e.g. processing data and controlling memory as well as all connected input and output devices. The processor will typically comprise one or more CPUs or microprocessors which may be supplemented by additional devices for support or control functions. Each of the components making up the processor circuitry may be special purpose or general purpose devices.

In exemplary embodiments the device is a drug delivery or drug dispensing device and the user-actuated operation is related to administration of a dose of a drug. The device may comprise a main portion with a drug reservoir and a drug administration mechanism, a cover portion releasably coupled to the main portion, and contact means arranged to detect when the cover is operated, such that the user-actuated operation is provided by operating the cover and actuating the contact means. The operation may e.g. be between a closed and an open state, between a closed and an open state, or between a locked and an un-locked state. The cover could e.g. be opened by a pivoting or sliding relative movement between the main portion and the cover, or the cover could be fully removable from the main portion. The user-actuated operation could also be the setting or expelling of a dose of drug. In a specific embodiment the user-actuated operation is the removal of a drug container from the main portion of the device.

Depending on the type of the device the electronic means for setting the reminders and detecting user-actuated operations could be arranged in different parts of the device. For example, for a mechanical device without "inherent" electronic means the electronic means for the reminder functionality could be located in a cover. In this way a basically mechanical device could be up-graded with reminder functionality in a simple and cost-effective way. On the other hand, if electronic means is already provided for other reasons, then the reminder functionality may be realized by utilizing these electronic means. For example, some drug injection devices are provided with an electronic display and/or memory, e.g. OptiClik™ from Aventis and HumaPen® Memoir™ from Lilly. Indeed, if the device is adapted to cooperate with a drug container like e.g. a tablet bottle then the electronic means will be located in the bottle receiving device.

Depending on the type of drug and the corresponding treatment regimen for a given patient the device may be set up to register a specific type of regimen. For example, the programming mode may be active to detect a single user-actuated operation at a given time of the day, whereby a daily reminder is provided at the detected given time of the day. This kind of functionality would for example be relevant for a diabetes drug which is to be taken once daily, e.g. Levemir® or Victoza® from Novo Nordisk. However, based on a single operation a week period a pre-programmed pattern of non-daily reminders could be provided at the detected given time of the day. For example, if a drug is to be taken three times per week operating the device on a Monday would automatically set reminders for Monday, Wednesday and Friday. Alternatively, the programming mode may be active to detect a number of user-actuated operations at given times of the day for a period of 24 hours, whereby daily reminders are provided corresponding to the detected given times of the day. This kind of functionality would for example be relevant for a diabetes drug which is to be taken e.g. three times daily in relation to a meal, e.g. NovoRapid® or NovoMix® from Novo Nordisk.

To avoid that the user has to set a clock, the reminders may be controlled by a non-real time clock, e.g. the clock may be a 24 hours clock which starts to run when the device is switched on for the first time or whenever the device is brought into programming mode. A given reminder may be muted when the corresponding user-actuated operation is performed within a pre-defined window of time in respect of the given reminder time. For example, if a reminder would sound at 8:00 corresponding to a breakfast meal then actuation of the device between 7:30 and 8:00 would cancel the 8:00 reminder. The reminder may be one of an acoustic, visual or tactile signal or a combination thereof.

To provide a simple and in-expensive device the means for detecting the user-actuated operation may also be used to bring the device into its programming mode. For example, the user may operate the device a number of times within a short period, e.g. the user may take off and put on a pen cap X times within Y seconds. To confirm that the device is now in its programming mode and all previous programming, if any, has been deleted the signal emitter may produce a special signal. In the same way, when the device automatically leaves the programming mode another signal may be used.

In the context of the present application and as used in the specification and claim, the term electronic means covers any combination of electronic circuitry suitable for providing the specified functionality, e.g. processing input data and controlling memory as well as all connected input and output devices. The electronic means may typically comprise one or more CPUs or microprocessors which may be supplemented by additional devices for support or control functions. For example, the sensor and output signal driver may be fully or partly integrated with the processor, or may be provided by individual units. Each of the components making up a processor circuitry may be special purpose or general purpose devices. A sensor for detecting when a user-actuated operation is performed may comprise a "sensor" per se, e.g. in the form of an electrical contact, or an optical or magnetic sensor capable of being influenced by the position of the other unit and adapted to produce a signal which can be recognized and processed by a processor. However, the sensor may also comprise or be associated with circuitry which detects and modifies a signal from a sensor per se before it is sent to the processor. Such circuitry may be formed integrally with a processor.

In a further aspect of the invention a method for programming reminders in an electronically controlled device is provided, comprising the steps of (a) providing an electronically controlled device having an operational mode in which reminders can be generated, the device being adapted to (i) be set in a programming mode by a user, (ii) to perform a user-actuated operation, (iii) detect when a user-actuated operation is performed, (iv) when in programming mode, record and set reminders in accordance with a detected pattern of operations of the device, the programming mode being activated for a pre-determined number of operations or for a pre-determined amount of time, where after the device automatically returns to an operational mode, (iv) provide reminders to the user in accordance with the recorded pattern of operations, (b) operating the device to bring the device in the programming mode, and (c) for the pre-determined number of operations or for a pre-determined period of time, perform one or more user-actuated operations.

As used herein, the term "drug" is meant to encompass any drug-containing medicine in the form of e.g. a liquid, a solution, a gel, a fine suspension, a powder or a gas. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of diabetes related drugs like insulins and GLP-1 like drugs.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Figure 1:
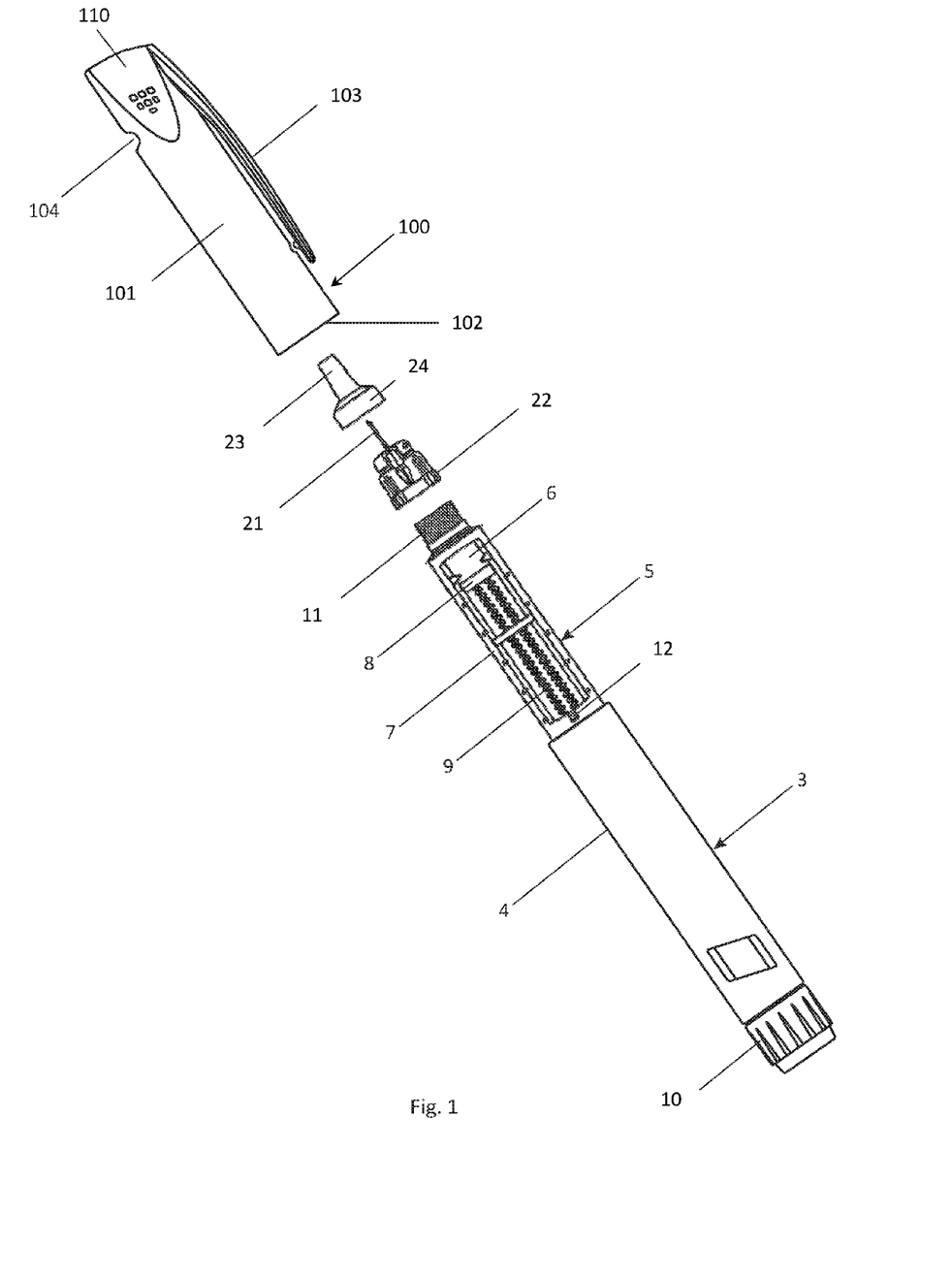
FIG. 1 shows an embodiment of a drug delivery pen comprising a pen cap.

Referring to FIG. 1 a pen-formed drug delivery device 1 will be described. The pen comprises a cap portion (or "pen cap") 100 and a main portion (or "pen body") 3 having a proximal part 4 in which a mechanical drug expelling mechanism is arranged, and a distal reservoir part 5 in which a drug-filled transparent cartridge 6 with a distal needle-penetratable septum is arranged and held in place by a cartridge holder 7 mounted to the proximal part, the cartridge holder having openings allowing a portion of the cartridge to be inspected. The cartridge is provided with a piston 8 driven by a piston rod 9 forming part of the expelling mechanism. A proximal-most button 10 serves to manually set and expel a desired dose of drug. This type of a pen-formed drug delivery device is well known, see e.g. WO 99/38554 to which reference is made for further details in respect of the internal construction of the shown type of pen. In the shown embodiment the pen is a disposable pre-filled device in which the cartridge holder is permanently attached to the proximal part of the main part, the cartridge holder being provided with distal coupling means in the form of an external thread 11 adapted to engage an inner thread of a needle assembly, see below. Alternatively the pen may be a "durable" device in which the cartridge holder is releasably attached to the main part, this allowing the piston rod to be pushed back and a new cartridge to be mounted. In such an arrangement the connection for the needle assembly may be part of the cartridge. The pen cap 100 comprises a generally cylindrical sleeve 101 with a proximal closed end and a distal opening 102, a pocket clip 103 and an opening 104 for a sound emitting transducer. The proximal end is provided with two opposed generally planar gripping surfaces 110. The pen cap further comprises electronic circuitry including an input sensor for detecting that the cap has been removed from the main portion as well as one or more signal generating devices (not shown). In the shown embodiment the contact means is arranged in the pen cap 100 cavity and actuated by a surface portion of the main portion (or "pen body") 3. The contact means may be of any desired nature such as a micro-switch or based on opto- or magneto-electronic means. The contact means may be operated just as the main portion (or "pen body") 3 is withdrawn or inserted into the cap 100 interior.

The electronic circuitry is adapted to provide the specified functionality, i.e. processing data from the sensor and controlling memory, providing time stamps as well as the signal generating means, e.g. a piezo buzzer, a LED and/or a vibrator. It is pointed out that an example of the present invention is embodied in the pen cap which is then adapted to be used in combination with one or more different pen main portions.

The time keeping means may be a quartz controlled clock device provided integrally with the controlling means in the form of a single integrated circuit (IC) which also comprises ROM memory for storing an executing program instructions as well as RAM memory for storing the different time stamps. The time keeping means may be operating as a normal real time clock (which then has to be set initially), however, the time keeping may be relative calculating the time merely from when the device is initiated, e.g. used for the first time.

FIG. 1 further shows a needle assembly comprising a hollow infusion needle 21 mounted in a cup-formed hub 22 with an inner coupling means in the form of a thread adapted to connect to the external thread 11 of the pen device. The needle comprises a distal pointed portion protruding from the hub as well as a proximal pointed portion adapted to penetrate the cartridge septum when the hub 22 is mounted on the thread 11. In an alternative embodiment a bayonet coupling may be used instead of the threaded connection, e.g. the cup may be provided with a plurality of inwardly projecting protrusions adapted to engage corresponding grooves formed distally on the pen device. The needle assembly further comprises a needle cap 23 with a skirt portion 24 adapted to releasably engage the hub to thereby protect the distal end of the needle.

The general idea of the invention is to provide an easy understandable and intuitive reminder programming functionality, where normal use of the drug delivery device provides automatic programming of a reminder scheme. The device may be intended to be used with a single type of drug, e.g. a diabetes drug which is to be taken once daily, e.g. Levemir® or Victoza® from Novo Nordisk, or a diabetes drug which has to be taken twice or more daily, e.g. NovoRapid® or NovoMix® from Novo Nordisk. Alternatively the device may be settable to be programmed in accordance with more than one type of regimen. Indeed, this would tend to make the device less intuitive and thus more complicated to use. In the following a number of examples illustrating different aspects of the present invention will be given.

EXAMPLE 1

A patient is in treatment for diabetes with a type of drug which is to be injected subcutaneously once daily, e.g. Levemir® or Victoza® from Novo Nordisk. The drug is injected using a pen-type injection device as shown in FIG. 1 and comprising a pen cap embodying an aspect of the present invention. The pen cap is specifically adapted for this type of treatment and thus to provide a reminder once every day at a given time. To program the pen cap the user will have to perform the following steps:

1) At the time of the day when the user in accordance with the prescribed regimen should take a dose of the drug (e.g. at 8:00 in the morning), the user sets the pen cap into programming mode, e.g. by taking off and putting on the cap 5 times within 3 seconds. To confirm that the pen cap is now in the programming mode a "program start" signal may be generated.

2) The user then takes off the pen cap, takes the prescribed dose of drug and puts on the pen cap again. By these actions programming has been done without the user having to do anything else. More specifically, the pen cap has now been programmed to provide a reminder every 24 hours starting from when the programming was done, i.e. at 8:00 in the morning every day.

EXAMPLE 2

A patient is in treatment for diabetes with a type of drug which is to be injected subcutaneously three times weekly, e.g. potential future long-acting versions of Levemir® or Victoza® from Novo Nordisk. The drug is injected using a pen-type injection device as shown in FIG. 1 and comprising a pen cap embodying an aspect of the present invention. The pen cap is specifically adapted for this type of treatment and thus to provide a reminder three times per week in accordance with a pre-determined regimen. To program the pen cap the user will have to perform the following steps:

1) At the time of the day and the day of the week when the user in accordance with the prescribed regimen should take a dose of the drug (e.g. at 8:00 Monday morning), the user sets the pen cap into programming mode as described for Example 1.

Figure 2:
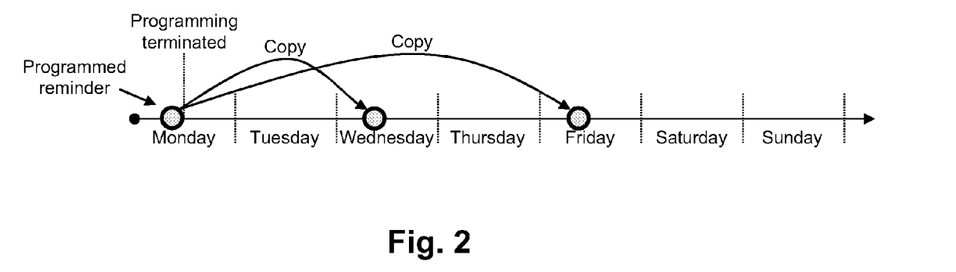
FIG. 2 shows a first programming example embodying the present invention.

2) The user then takes off the pen cap, takes the prescribed dose of drug and puts on the pen cap again. By these actions programming has been done without the user having to do anything else. More specifically, the pen cap has now been programmed to provide a reminder at 8:00 in the morning Monday, Wednesday and Friday, see FIG. 2 in which "programmed reminder" means the actual programming done by the user, "programming terminated" means the automated end of the programming mode (here at the end of a single action), and "copy" means the automatic programming taking place in accordance with the pre-programmed set-up of the actual pen.

EXAMPLE 3

A patient is in treatment with a type of drug which is to be injected subcutaneously a number of times per day every day, e.g. twice daily. The drug is injected using a pen-type injection device as shown in FIG. 1 and comprising a pen cap embodying an aspect of the present invention. The pen cap is specifically adapted for this type of treatment and thus to provide reminders every day at given times. To program the pen cap the user will have to perform the following steps:

1) At the time of the day when the user in accordance with the prescribed regimen should take a first dose of the drug (e.g. at 8:00 in the morning), the user sets the pen cap into programming mode as described for Example 1.

Figure 3:
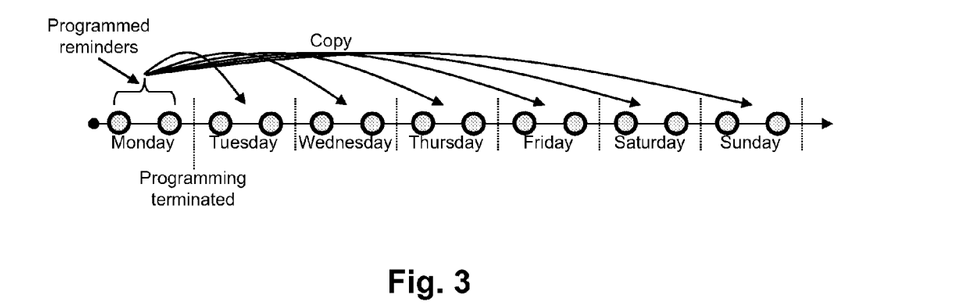
FIG. 3 shows a second programming example embodying the present invention.

2) The user then takes the prescribed doses of drug in accordance with the prescribed regimen (e.g. at 8:00 in the morning and 8:00 in the evening). By these actions programming has been done without the user having to do anything else. More specifically, the pen cap has now been programmed to provide a reminder at 8:00 in the morning and 8:00 in the evening every day, see FIG. 3 in which the automatic "programming terminated" is controlled by time.

EXAMPLE 4

A patient is in treatment for diabetes with a type of drug which is to be injected subcutaneously once daily, e.g. Levemir® or Victoza® from Novo Nordisk. The drug is injected using a pen-type injection device as shown in FIG. 1 and comprising a pen cap embodying an aspect of the present invention, however, in contrast to Example 1 the patient prefers a regimen in which the dose of drug is not taken at the same time every day but is tailored to match the patient's personal preferences. The pen cap is specifically adapted for this type of treatment and thus to provide reminders which vary from day to day but is the same from week to week. To program the pen cap the user will have to perform the following steps:

1) At the day and time when the user in accordance with the prescribed regimen should take a first dose of the drug, the user sets the pen cap into programming mode as described for Example 1.

Figure 4:
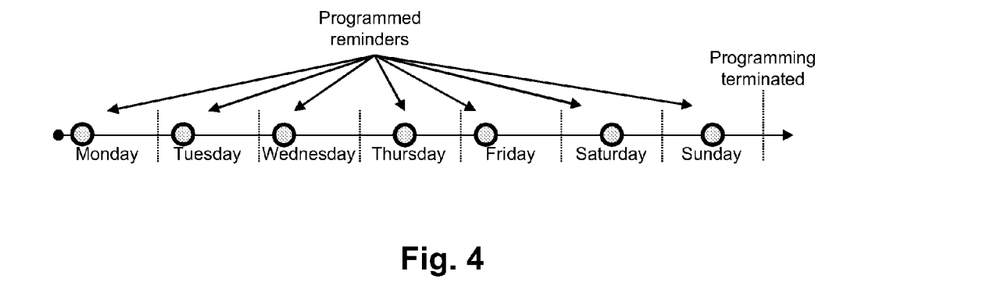
FIG. 4 shows a third programming example embodying the present invention.

2) The user then takes the prescribed doses of drug in accordance with the prescribed regimen for 7 days (e.g. once every day between 6:00 in the morning and noon). By these actions programming has been done without the user having to do anything else. More specifically, the pen cap has now been programmed to provide a daily reminder in accordance with the patient's preferred time schedule, see FIG. 4 in which no automatic "copy" takes place. Indeed, the pen cap could also be adapted to allow the programming of a number of individual reminders for each of the weekdays.

For the above examples, to avoid accidental programming the pen cap electronics may be programmed to require a given number of seconds to pass between the off-ons of the pen cap to count as programming relevant user-actuated operation, e.g. minimum 6 seconds, this indicating that a dose of drug has been injected. Further, the pen cap may be provided with a mute function as described above.

Figure 5:
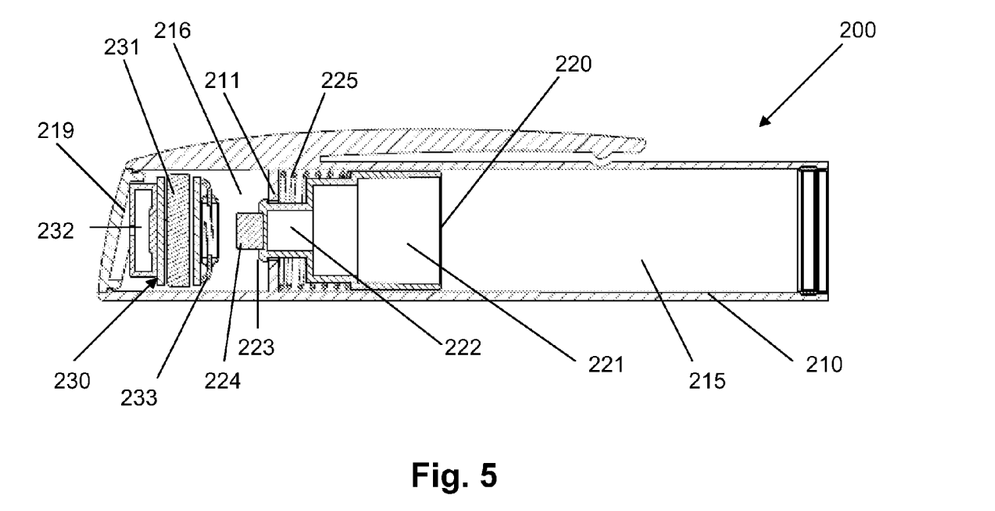
FIG. 5 shows a first embodiment of a pen cap comprising electronic means.
Figure 6:
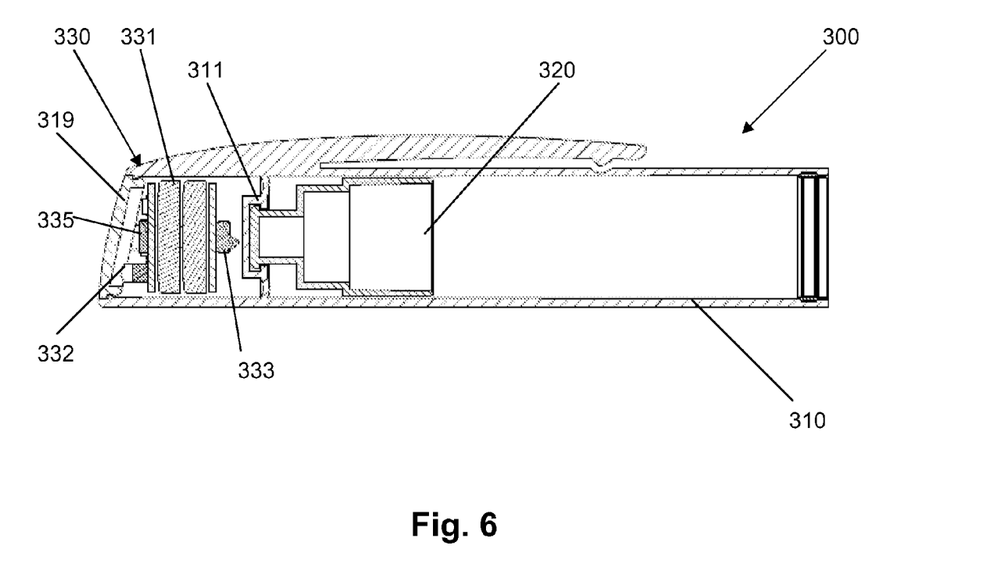
FIG. 6 shows a second embodiment of a pen cap comprising electronic means.

With reference to FIGS. 5 and 6 schematic representations of embodiments of the invention will be described.

FIG. 5 shows a pen cap 200 having the same general appearance as pen cap 100 in FIG. 1 and is adapted to be used with a pen body having a general design as the pen body 3 shown in FIG. 1. The pen cap 200 comprises a housing 210 with an inner partition wall 211 dividing the interior of the cap in a proximal cavity 215 adapted to receive a distal portion of a pen body with a mounted needle assembly, and a distal cavity 216 closed with a distal lid member 219, the wall having a central opening adapted to receive and hold an actuation member 220. The actuation member comprises a proximal skirt portion 221 adapted to receive and engage a needle assembly, and a distal cylindrical portion 222 adapted to be received in sliding engagement in the central opening of the wall partition, the cylindrical portion being provided with a distal circumferential flange 223 adapted for locking engagement with the central opening as well as a small magnet 224. Between the partition wall and the skirt portion a spring 225 is arranged to bias the actuation member in a proximal direction. The skirt portion and/or the cylindrical portion are adapted to provide a seal between the two cavities, this preventing e.g. fluid from entering the distal cavity.

In the distal cavity the electronic means 230 providing the reminder functionality of the cap is arranged, the electronic means comprising a processor and associated memory (not shown), an electric cell 231 ("battery"), a buzzer 232 and a read switch 233 which is actuated when the actuation member is moved distally when a pen body is inserted in the proximal cavity of the pen cap. Depending on the specific design of the actuation member, actuation of the read switch may or may not require that a needle assembly is mounted on the pen body.

FIG. 6 shows a pen cap 300 having the same general design as pen cap 200 described above, however, the actuation member 320 is fixedly locked to a flexible partition wall 311 which both allows axial travel of the actuation member and provides a proximal-directed spring force on the actuation member. The flexible partition wall may be formed integrally with the pen cap housing 310 as shown, or may be a separate member mounted in the housing. The electronic means 330 comprises a processor 335 and associated memory, two electric cells 331, a LED 332 and a mechanical switch 333 which is actuated when the actuation member 320 is moved distally. The distal lid member 319 is transparent allowing a user to observe the LED. The electronic means may also be provided with communication means, e.g. an IR LED or a radio transmitter, allowing communication between the pen cap electronics and an external system, e.g. a PC at the doctor's office.

In the above a pen-formed drug delivery device is used to illustrate different examples embodying aspects of the present invention, however, the invention may be used in many other types of devices, e.g. medical aerosol inhalers, tablet dispensing devices and blood glucose meters etc.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An electronically controlled drug delivery device having an operational mode in which reminders can be generated, the device comprising:
   a main portion comprising a drug reservoir and a drug administration mechanism,
   a cover portion releasably coupled to the main portion,
   electronic circuitry comprising a processor and associated memory, the device being adapted to perform a user-actuated operation related to administration of a dose of a drug, and the electronic circuitry being adapted to:
   be set in a programming mode by a user in which reminders can be automatically programmed into the device,
   receive a signal that a user-actuated operation related to administration of a dose of a drug is performed,
   when in programming mode, record and set reminders in accordance with a detected time pattern of user-actuated operation(s) of the device that cause administration of a dose of a drug, and
   provide reminders to the user based on the detected time pattern of user-actuated operations,
   wherein the programming mode is activated for a pre-determined number of user-actuated operations or for a pre-determined period of time, whereafter the device automatically returns to the operational mode in which reminders can be generated.

2. An electronically controlled drug delivery device as in claim 1, wherein the device comprises:
   contact structure arranged to detect when the cover portion is operated,
   wherein the user-actuated operation is provided by operating the cover portion.

3. An electronically controlled drug delivery device as in claim 2, wherein the electronic circuitry is located in the cover portion.

4. An electronically controlled drug delivery device as in claim 1, wherein the programming mode is active to detect a single user-actuated operation at a given time of the day, whereby a daily reminder is provided at the detected given time of the day.

5. An electronically controlled drug delivery device as in claim 1, wherein the programming mode is active to detect a number of user-actuated operations at given times of the day for a period of 24 hours, whereby daily reminders are provided corresponding to the detected given times of the day.

6. An electronically controlled drug delivery device as in claim 1, wherein the programming mode is active to detect a single user-actuated operation at a given time of the day, whereby for a week period a pre-programmed pattern of non-daily reminders is provided at the detected given time of the day.

7. An electronically controlled drug delivery device as in claim 1, further comprising non-real time clock structure for controlling the reminders.

8. An electronically controlled drug delivery device as in claim 1, wherein a given reminder can be muted when the corresponding user-actuated operation is performed within a pre-defined window of time in respect of the given reminder time.

9. An electronically controlled drug delivery device as in claim 1, wherein the reminders are acoustic, visual and/or tactile signals.

10. A method of programming reminders in an electronically controlled drug delivery device, comprising the steps of:
    performing, with the electronically controlled drug delivery device, a user-actuated operation related to administration of a dose of a drug,
    wherein the electronically controlled device has a programming mode in which reminders can be automatically programmed into the device, and an operational mode in which the programmed reminders can be generated, the device being adapted to:
    be set in the programming mode by a user in which reminders can be automatically programmed into the device,
    detect when a user-actuated operation related to administration of a dose of a drug is performed, and when in the programming mode, record and set reminders in accordance with a detected pattern of user-actuated operations of the device that cause administration of a dose of a drug, the programming mode being activated for a pre-determined number of user-actuated operations or for a pre-determined amount of time whereby reminders can be automatically programmed into the device, whereafter the device automatically returns to the operational mode.

* * * * *